US00PP20939P2

(12) United States Plant Patent
Gessell

(10) Patent No.: US PP20,939 P2
(45) Date of Patent: Apr. 20, 2010

(54) ***LONICERA* PLANT NAMED 'BAILELLE'**

(50) Latin Name: *Lonicera×brownii*
Varietal Denomination: Bailelle

(75) Inventor: Steve Gessell, St. Cloud, MN (US)

(73) Assignee: Bailey Nurseries, Inc., New Port, MN (US)

( * ) Notice: Subject to any disclaimer, the term of this patent is extended or adjusted under 35 U.S.C. 154(b) by 0 days.

(21) Appl. No.: 12/381,283

(22) Filed: Mar. 10, 2009

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
(74) *Attorney, Agent, or Firm*—Penny J Aguirre

(57) ABSTRACT

A new cultivar of *Lonicera×brownii,* 'Bailelle', characterized by its dense flowering display of inflorescences in June with consistent repeat bloom into September and October, its flowers that are deep gold in color, its compact twining plant habit, its vigorous growth and ability to grow in a wide range of growing conditions with drought and moisture tolerance, its ability to attract hummingbirds and butterflies, and its hardiness in U.S.D.A. Zones 3 to 8.

2 Drawing Sheets

Botanical classification: *Lonicera×brownii.*
Variety denomination: 'Bailelle'.

BACKGROUND OF THE INVENTION

The present invention relates to a new and distinct cultivar of *Lonicera×brownii* will be referred to hereafter by its cultivar name, 'Bailelle'. 'Bailelle' is a new cultivar of Brown's Honeysuckle, a vine grown for use as an ornamental landscape plant for its funnel-shaped flowers, deep green leaves and ability to cover walls and trellises.

The Inventor discovered 'Bailelle' as a naturally occurring branch mutation of *Lonieraxbrownii* 'Dropmore Scarlet' (not patented) in the summer of 2003 in a cultivated garden in St. Cloud, Minn.

Asexual reproduction of the new cultivar was first accomplished under the direction of the Inventor using softwood stem cuttings in summer of 2004 in St. Paul, Minn. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for four years in St. Paul, Minn. These attributes in combination distinguish 'Bailelle' as a unique cultivar of Brown's Honeysuckle.

1. 'Bailelle' exhibits flowers that are deep gold in color.
2. 'Bailelle' exhibits a dense flowering display of inflorescences that about 6.35 to 7.62 cm in diameter on mature plants.
3. 'Bailelle' produces a heavy flush of flowers in June and has consistent re-bloom into September and October.
4. 'Bailelle' is has a vigorous growth rate and forms a compact, twining vine that reaches 3 to 6 m in length.
5. 'Bailelle' is hardy in U.S.D.A. Zones 3 to 8, is drought and moisture tolerant, and will tolerate a wide range of growing conditions.
6. 'Bailelle' attracts hummingbirds and butterflies.

'Bailelle' can be compared to *Lonicera×brownii* 'Dropmore Scarlet', the parent plant. 'Dropmore Scarlet' differs from 'Bailelle' in producing flowers that are orange-red in color and in having slightly smaller inflorescences. 'Bailelle' can also be compared to 'Kristin's Gold' (U.S. Plant Pat. No. 12,836), which is also a branch mutation of 'Dropmore Scarlet', 'Kristin's Gold' has flowers that are bright yellow in color. 'Bailelle' can also be compared to the *Lonicera×brownii* cultivars 'Minstrum' and 'Toison dOr' (both unpatented). 'Minstrum' differs in having flowers that are copper-yellow in color, and 'Toison dOr' differs in having flowers that are clear yellow in color.

BRIEF DESCRIPTION OF THE DRAWING

The accompanying colored photographs were taken in mid summer and illustrate the overall appearance and distinct characteristics of 6 year-old plants the new *Lonicera* as grown in a trial garden in St. Paul, Minn.

The photograph in FIG. 1 provides an overall view of the growth habit and blooming habit of 'Bailelle'.

Figure 1:
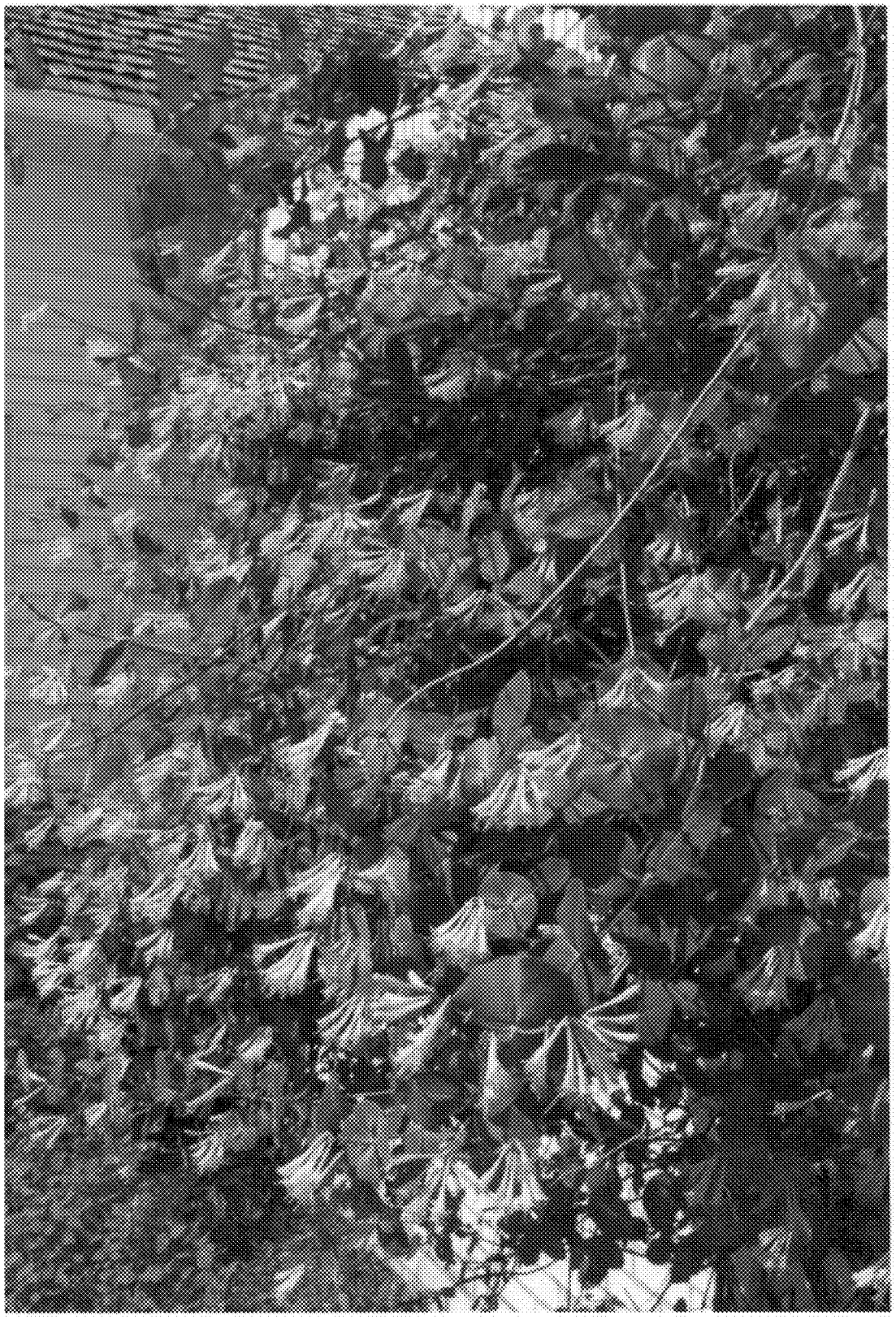
Figure 2:
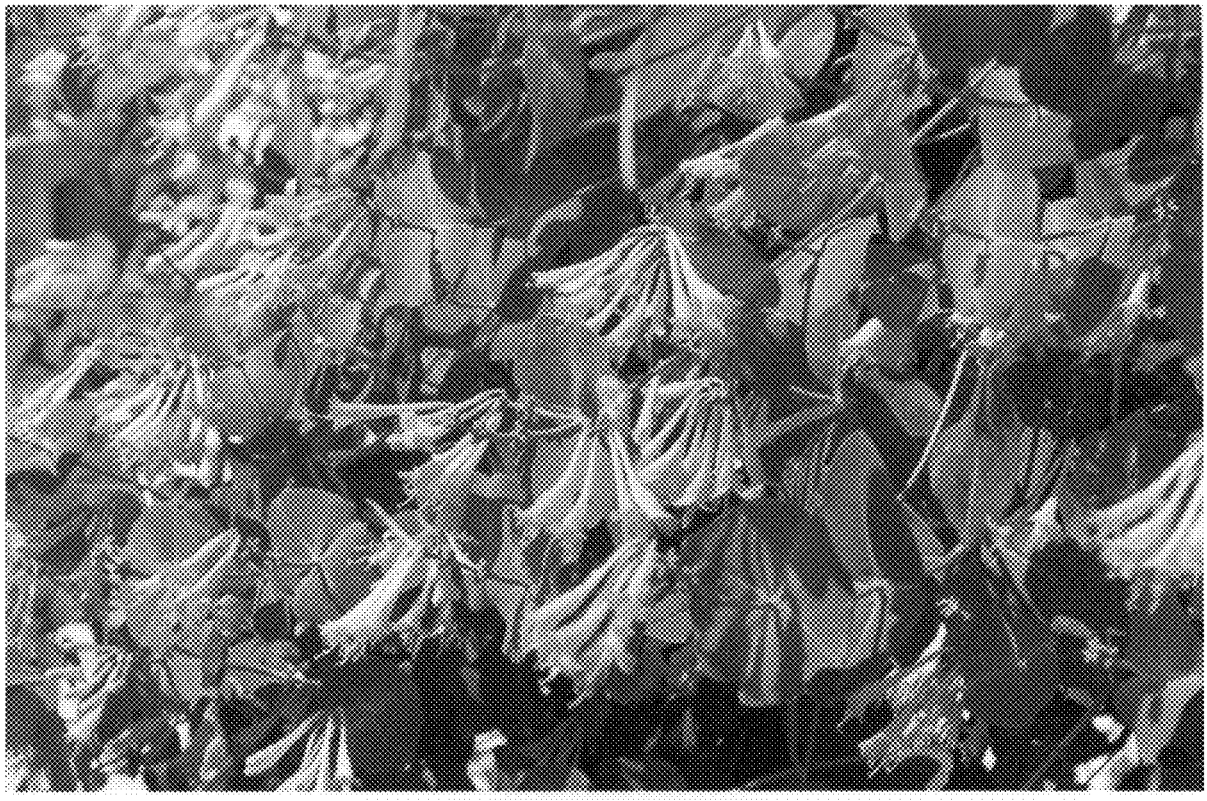

The photograph in FIG. 2 provides a close-up view of the inflorescences of 'Bailelle'.

The colors in the photographs may differ slightly from the color values cited in the detailed botanical description, which accurately describe the colors of the new *Lonicera.*

DETAILED BOTANICAL DESCRIPTION

The following is a detailed description of 6 year-old plants of the new cultivar as grown outdoors in full sun in a trial plot in St. Paul, Minn. with the detailed foliage and flower data collected on 3 year-old plants as grown outdoors in two-gallon containers in St. Paul, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Blooms heavily in June with consistent repeat bloom continuing into September and October.

*Plant habit.*—Compact twining vine, growth is prostrate unless supported.

*Length.*—Reaches 3 to 6 m in length.

*Hardiness.*—U.S.D.A. Zones 3 to 8.

*Diseases and pests.*—No susceptibility or resistance to diseases or pests has been observed.

*Culture.*—Grows in wide range of soil conditions in full sun, drought and moisture tolerant, will tolerate semi-shade but flowering performance is best in full sun.

*Root description.*—Fibrous.

Growth and propagation:

*Propagation.*—Terminal, softwood stem cuttings.

*Growth rate.*—Vigorous.

Stem description:

*Shape.*—Oval.

*Stem color.*—New growth; 145A, mature wood; 199B becoming bark with striations of 199B and N200A.

*Stem size.*—Stem base; about 2.5 cm diameter and length, lateral woody branches; an average of 5 mm in width and indeterminate in length, new growth; average of 2 mm in diameter and an average of 25 cm in length on 3 months of growth.

*Stem surface.*—New growth; Glabrous and slightly glaucous, mature wood is dull and smooth and becoming bark-like and ridged as it ages.

*Internode length.*—Whorls near base.

*Branching.*—Average of 10 lateral woody branches with new growth emerging in opposite arrangement from axillary nodes; about 20 per plant in a 2 gallon container.

Foliage description:

*Leaf shape.*—Oval to broadly elliptic with terminal leaves fused and oval to deltoid.

*Leaf division.*—Simple.

*Leaf base.*—Cuneate and fused on terminal leaves (1 to 2 pairs) before inflorescence.

*Leaf apex.*—Rounded with some leaves having a small single notch at apex.

*Leaf fragrance.*—None.

*Leaf venation.*—Pinnate, somewhat conspicuous but not prominent, color on upper surface, 144B, color on lower surface; 144C to 139D.

*Leaf margins.*—Entire.

*Leaf arrangement.*—Opposite.

*Leaf attachment.*—Petiolate with terminal fused pairs perfoliate.

*Leaf surface.*—Glabrous on upper surface and glaucous on lower surface.

*Leaf internode length.*—Ranges from 2 to 5 cm with an average of 3.7 cm.

*Leaf size.*—Up to 8 cm in length and 5 cm in width with terminal fused pairs up to 4.5 cm in length and 5.5 cm in width (each).

*Leaf quantity.*—Average of 6 pair per branch 32 cm in length.

*Leaf color.*—Newly expanded leaves; upper surface 144A, lower surface 138A, mature leaves; upper surface 137A to N137A, lower surface color 138A with glaucous coating of 191C, fall leaves; not distinguishable from mature foliage.

*Petioles.*—About 5 mm in length and 2 mm in width, color is 144A on upper surface and 144B on lower surface, glabrous surface.

*Stipules.*—Typically 2 per leave, held together and upright on stem, lanceolate in shape, glabrous surface, about 2 mm in length and 1 mm in width, 144D in color on both surfaces.

Inflorescence description:

*Inflorescence type.*—Comprised of 2 to 3 whorls of tubular flowers at terminus of new growth, 5 flowers per whorl.

*Inflorescence size.*—Average of 5 cm in length and 5.7 cm in diameter on plants grown in a 2-gallon container, on mature plants in the landscape; inflorescences are larger and range from 6.35 to 7.62 in diameter with an average of 5.8 cm in length.

*Flower buds.*—Oblanceolate in shape, upper half 13A in color narrowing to tube 12C in color with the base slightly suffused with 144C, an average of 3.5 cm in length and 5 mm in width (near apex).

*Flower fragrance.*—None detected.

*Lastingness of inflorescence.*—Inflorescence blooms for 2 to 3 weeks with individual flowers lasting about 4 days, lower whorls begin opening first.

*Flower quantity.*—10 to 15 flowers per inflorescence (5 per whorl), about 200 per plant grown in a 2-gallon container.

*Flower type.*—Tubular, somewhat 2-lipped.

*Flower size.*—Average of 1.5 cm in diameter and 4 cm in depth (including exserted stamens and pistil).

*Peduncles.*—Average of 2.5 cm in length to base of inflorescence and 2 mm in diameter and an average of 6 mm in length and 2 mm in width between whorls, 145A to 145A blended with 138A in color, glaucous surface, oval in shape.

*Bracts.*—2, at base of each whorl, held horizontal, broadly lanceolate in shape, 145D in color, glaucous surface, acute apex, truncate base, about 1 mm in width at base and 1.5 mm in length.

*Pedicels.*—None, sessile to peduncle.

*Calyx.*—5 starred, 1.5 mm in diameter and 0.5 mm in depth.

*Sepals.*—5, un-fused portion in triangular shape, acute apex, fused base, 144D in color, membranous surface with apex region membranous, about 0.5 mm in length and 0.3 mm in width on unfused portion, entire margin.

*Petals.*—5, fused into tube with apex of each free, fused portion is about 3 cm in length and 5 mm in width near apex, free portion is somewhat 2-lipped with upper lip comprised of 4 petals flared outward and lower lip comprised of 1 petal that is reflexed, free portion of upper lip petals are triangular in shape and about 3 mm in length and width, free portion of lower lip petal is oblong in shape about 7 mm in length and 4 mm in width, all free petals portions have a broadly acute apex and entire margin, outer and inner surface is glabrous, color of inner and outer surface is 13A with base 13C, non fading and self cleaning.

Reproductive organs:

*Gynoecium.*—1 pistil, about 4.3 cm in length with about 6 mm exserted beyond corolla, style is about 3.9 cm in length, very fine, and 151D in color, stigma is about 1 mm in diameter and 0.7 mm in width, flattened globose in shape and N144A in color, ovary is inferior, ovoid in shape, about 3 mm in length and 2 mm in diameter and 144A in color.

*Androcoecium.*—5 stamens, about 4 cm in length with about 5 mm exserted beyond corolla, filaments are 4B in color, about 3.9 mm in length, very fine with lower half adnate to tube, anthers are about 2.5 mm in length, N199B in color and dorsifixed, pollen is abundant in quantity and 14D in color.

*Fruit and seed.*—Fruit sparsely produced, true berry, round in shape, about 7 mm in diameter, produced in fall, about 42A to 42B in color, seldom produced under nursery production.

It is claimed:

1. A new and distinct cultivar of *Lonicera* plant named 'Bailelle' as herein illustrated and described.

* * * * *